United States Patent [19]

Loch

[11] 4,051,719

[45] Oct. 4, 1977

[54] METHOD AND APPARATUS FOR THE MOISTURE MEASUREMENT OF FLAT STRUCTURES, ESPECIALLY TEXTILE WEBS

[75] Inventor: Ernst Loch, Uster, Switzerland

[73] Assignee: Zellweger Uster AG, Uster, Switzerland

[21] Appl. No.: 714,858

[22] Filed: Aug. 16, 1976

[30] Foreign Application Priority Data

Oct. 20, 1975 Switzerland .................. 13571/75

[51] Int. Cl.² ........................................ G01N 25/56
[52] U.S. Cl. .................................................. 73/73
[58] Field of Search ............... 73/73, 159; 162/263; 324/65 R

[56] References Cited

U.S. PATENT DOCUMENTS

| | | | |
|---|---|---|---|
| 2,484,594 | 10/1949 | Spangenberg | 324/65 R X |
| 2,942,352 | 6/1960 | Eicken | 324/65 R X |

*Primary Examiner*—Jerry W. Myracle
*Attorney, Agent, or Firm*—Werner W. Kleeman

[57] ABSTRACT

A method of, and apparatus for, measuring the moisture content or dampness of flat structures, especially textile webs, wherein the flat structure has electrical charges withdrawn therefrom prior to initiating the measuring operation.

3 Claims, 5 Drawing Figures

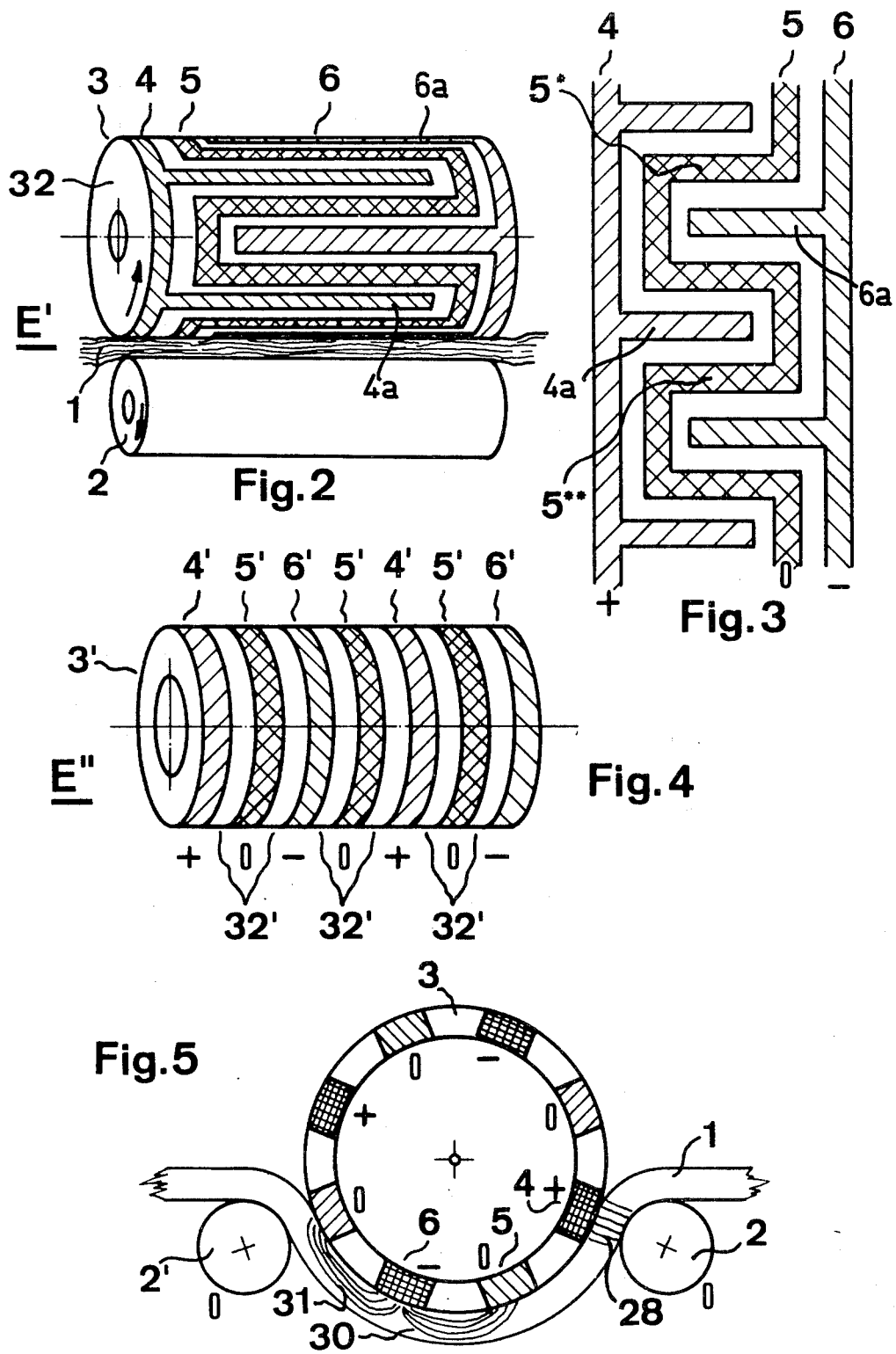

METHOD AND APPARATUS FOR THE MOISTURE MEASUREMENT OF FLAT STRUCTURES, ESPECIALLY TEXTILE WEBS

BACKGROUND OF THE INVENTION

The present invention relates to a new and improved method of, and apparatus for, measuring the moisture content or dampness of flat textile structures, especially textile webs.

The heretofore known textile moisture regulators which perform moisture measurements according to a conductance measurement principle only can fulfill their function in a limited fashion, especially since the advent of synthetic textile fibers. Thus, the conventional input circuit, constituted by a voltage divider composed of the oftentimes extremely high current-flow resistance of the textile web to be measured and a limited high ohm fixed resistor, no longer furnishes any practically usable signal evaluation at voltage divider ratios greater than approximately 1:100 and 100:1.

The resistance values up to about $10^{12}$ ohms which are conventional for synthetic textiles lead to voltage divider ratios which are larger by a number of decades than the indicated values. Also a corresponding increase of the fixed resistance of the aforementioned voltage divider, as a general rule, is hardly possible due to the limited insulation properties of the insulation material which is employed and the input resistance of the required measuring amplifier.

Apart from these limitations of the measurement range, there are also present disturbance effects caused by external voltages, thus, for instance, due to electrostatic charges especially present in the case of textile webs formed of synthetic fibers, but furthermore also due to noise or hum. Fault currents, caused by such external voltages, are often of the same order of magnitude or even greater than the measurement currents of a number of picoamperes which are standard in the case of dry, synthetic textiles and thus render impossible reliable measurement of such materials.

SUMMARY OF THE INVENTION

Hence, it is a primary object of the present invention to provide a new and improved method of measuring the moisture content or dampness of flat textile structures, especially textile webs and an apparatus for the performance of the aforesaid method, wherein the disturbing effects impairing the measuring reliability are avoided or at least their effect reduced.

The method of the present invention for the measurement of the moisture content of flat textile structures, especially textile webs, is manifested by the features that electrical charges are withdrawn from the test material prior to initiation of the measurement operation.

The apparatus for the performance of the aforementioned method aspects comprises an electrode arrangement in contact with the test material, the electrode arrangement possessing, in addition to the measuring electrodes for the moisture measurement, at least one discharge electrode neighboring such measuring electrodes.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 2 illustrates a construction of an electrode arrangement;

FIG. 3 is a development of the electrode arrangement according to FIG. 2;

FIG. 4 illustrates a further construction of the electrode arrangement; and

FIG. 5 is a sectional view through the apparatus of FIG. 2.

DETAILED DESCRIPTION OF THE PREFERRED EMBODIMENTS

Figure 1:
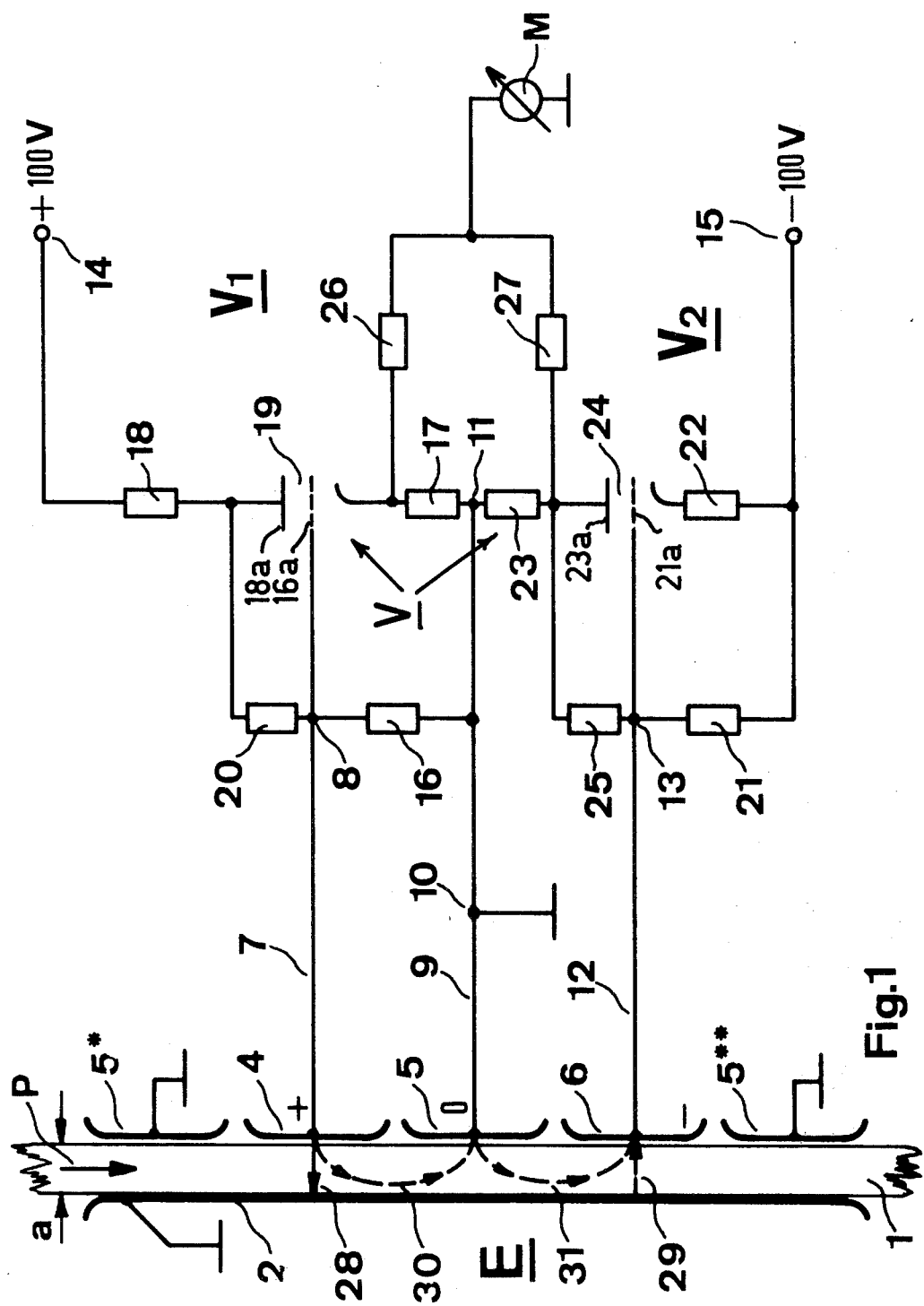
FIG. 1 schematicaly illustrates an apparatus constructed according to the invention for explaining the principle of operation, the illustration not being to scale.

Describing now the drawings, it is to be understood that throughout the various Figures the same or analogous components have been designated by the same reference characters and that the various Figures have not been drawn to scale. FIG. 1 illustrates, for the purpose of explaining the operating principle of the invention, a schematically illustrated embodiment of inventive apparatus. The flat textile structure, here in the form of a band-shaped textile material, also referred to as the test material 1, of the thickness $d$, for instance a textile web, passes through an electrode arrangement E and thus contacts, with its one surface, a first electrode 2 connected with ground or earth. Electrode 2 carries zero potential. The test material 1 contacts with its opposite surface at a series of additional electrodes 4, 5 and 6. As to these additional electrodes the electrode 4 is supplied via the line or conductor 7 with a positive potential, the electrode 5 via the conductor or line 9, from the ground point 10, with ground potential, and the electrode 6 via a conductor or line 12 is supplied with negative potential.

The conductor 7 leads from the electrode 4 to a first input 8 of an amplifier arrangement V. From the further or additional electrode 5 the conductor 9 leads via the ground point or terminal 10 to a center point or tap 11 of the amplifier arrangement V. The conductor or line 12 leads from the further electrode 6 to a second input 13 of the amplifier arrangement V.

The amplifier arrangement V is characterized by the fact that it has two direct-current series connected partial amplifiers $V_1$ and $V_2$. At a terminal 14 there is delivered to the amplifier arrangement V a positive supply voltage, for instance +100 volts, and at a terminal 15 there is delivered a negative supply voltage, for instance −100 volts.

For instance, the amplifier arrangement V, as illustrated in FIG. 1, can be constructed as a tube amplifier, but it is also possible to select a semiconductor-amplifier arrangement, preferably such having a field-effect transistor input. Of course, in this case there are to be selected in conventional fashion suitable supply voltages.

With the amplifier arrangement V the partial amplifier $V_1$ possesses a grid resistor 16, a cathode resistor 17, an anode resistor 18 and a feedback resistor 20 between the anode 18a and grid 16a of the amplifier tube 19. In analogous manner the partial amplifier $V_2$ possesses a grid resistor 21, a cathode resistor 22, an anode resistor 23 and a feedback resistor 25 arranged between the anode 23a and grid 21a of the amplifier tube 24.

The output signal of the partial amplifier $V_1$ and the output signal of the partial amplifier $V_2$ are each delivered via a respective resistor 26 and 27 to a measuring element M. The measuring element M has delivered thereto the sum of both output signals. The measuring element M also can be combined with a regulation element, itself can be constructed as a regulation element, or the amplifier arrangement V can have connected following the same a conventional regulation device having the function of controlling regulation operations for influencing the test material 1 in accordance with the measurement value delivered by the amplifier arrangement V.

Due to the potential applied to the electrode arrangement E there are formed electrical fields at the test material 1 which produce currents flowing between the individual electrodes. These currents and the voltage drop caused by the same are delivered to the amplifier arrangement V for further processing. The magnitude of the currents flowing through the test material 1 is predominantly dependent upon its moisture content, so that the currents and the voltage drop resulting therefrom, appearing at the electrode arrangment E, constitutes a measure for the degree of moisture contained in the test material 1. In the case of relatively dry test material such is quite high ohmic and there appear resistance values up to about $10^{12}$ ohms between the individual electrodes of the electrode arrangement E. Such high ohm characteristic of the test material causes difficult problems for the measuring operation insofar as a result thereof there can easily arise disturbance voltages which detrimentally affect or disturb the measuring operation. Thus, there appear at the text material 1, namely when it contains synthetic fibers, oftentimes electrical charges of considerable potential. For removing such disturbing charges the electrode arrangement E, according to the showing of FIG. 1, possesses at least at the input side of the test material 1 moving in the direction of the arrow P relative to the electrode arrangment E, a grounded discharge electrode 5*.

In this way there is achieved the result that electrical charges appearing at the test material 1 are withdrawn therefrom before such test material enters the measuring zone, i.e. the region of the further electrodes 4, 5 and 6. In this way there is effectively avoided the appearance of fault currents which would otherwise arise in the absence of such discharge electrode 5* and which would impair the measuring operation.

Owing to the high-ohm characteristics of the measuring arrangment there also exists the danger of entry of noise or ripple voltages due to the action of electrical installations located at the surroundings. It has been found that the electrode 5* also contributes to the electrostatic screening of the measuring zone at the region of the electrodes 4 to 6, especially if an additional grounded discharge electrode 5** is arranged neighboring the further electrode 6.

With the measuring arrangement according to FIG. 1 the measurement signals decisive for the moisture content of the test material 1 assist the direct-current flow through the amplifier arrangement V and thus produce an output signal at the measuring element M, whereas the aforementioned disturbing influences produce measuring signals which, with respect to their control action upon the current flow, are oppositely directed through the amplifier arrangment and thus extensively eliminated.

The invention also affords the decisive advantage that it is immune against disturbing influences of the aforementioned type and nonetheless possesses a measuring sensitivity which is sufficient for the practically extremely high ohm test material. This advantage is achieved by virtue of the fact that the electrode arrangement E constitutes a push-pull arrangement and the amplifier arrangement V acts in an additive manner with regard to the measuring signals from the further electrodes 4 and 6 and thus, the useful signal components which change in the same direction are employed for the indication, whereas the disturbance voltages dependent upon the external voltages and effective in opposed directions are extensively eliminated. Due to the potential applied to the further electrodes 4, 5 and 6 there is formed an electrical field 28 between the electrode 4 and the electrode 2 which extends transversely through the test material 1 and an electrical field 29 between the electrode 2 and the electrode 6 which likewise extends transversely through the test material. Due to the currents caused by such fields, useful signals appear at the electrodes 4 and 6 constituting a measure for the moisture content of the test material 1. These useful signals are delivered via the lines or conductors 7 and 12 to the first input 8 and the second input 13, respectively, of the amplifier arrangement V.

It should be readily appreciated that owing to the polarities selected for the present measuring arrangement the useful signals at the electrodes 4 and 6 assist one another with respect to the direct-current flow through the amplifier arrangement V. Owing to the potentials appearing at the electrodes 4, 5 and 6 there are also, however, formed the electrical fields 30 and 31 which extend in the lengthwise direction of the test material 1. It is readily apparent that by virtue of such fields 30 and 31 there also appear useful signals which are added to the measuring signals produced by the fields 28 and 29. With a measuring arrangement according to FIG. 1 the test material 1 therefore is measured both in transverse direction as well as also in lengthwise direction. In so doing, it is to be observed that the conductance or specific conductivity of the test material 1 in the direction of the fields 28 and 29 decreases with increasing thickness $d$, but however the conductance or specific conductivity of the test material 1 in the direction of the fields 30 and 31 increases with increasing thickness $d$. By optimizing the dimensions of the electrical arrangement E it is therefore possible to approximately compensate, at least throughout a certain range, the influence of the thickness $d$ of the test material upon the measuring value finally delivered by the measuring arrangement. Also this constitutes a decisive advantage of the invention.

There are possible further advantageous constructions of the invention which will be explained based upon the additional Figures hereinafter.

In FIG. 2 there is shown the configuration of an electrode arrangement E'. Again in FIG. 2 the test material is designated by reference character 1, the ground electrode by reference character 2. There also can be provided more than one ground electrode 2. The ground electrode 2 is constructed as a cylinder mounted for rotation about its lengthwise axis, rotating in the direction of the indicated arrow and arranged below the test material 1. Above the test material 1 there is arranged a cylinder 3 mounted to be rotatable about its lengthwise axis in the direction of the arrow shown, this cylinder 3 consisting of a cylinder-shaped insulating element 32 and at its jacket surface or shell further electrodes 4, 5 and 6 which have been applied for instance by a galvanic process. The further electrodes 4 and 6 are of comb-like configuration having the combs 4a and 6a respectively, arranged offset with respect to one another and aligned to confront one another. In the intermediate spaces which are formed between the comb teeth 4a, 6a there is located a meander-shaped ground electrode 5.

In order to clarify the illustration of this arrangement there has been depicted in FIG. 3 a development of the cylinder 3. The individual electrodes 2, 4, 5 and 6 have delivered thereto, in conventional manner, for instance through the aid of sliding contact or slip rings, the potentials required as shown in FIG. 1 and previously disclosed. Hence, this has not been particularly shown in FIG. 2 in order to preserve clarity in illustration.

In accordance with the direction of rotation of the cylinder-shaped ground electrode 2 and the cylinder 3, indicated by the arrows, the test material 1 moves from the rear towards the front through the measuring arrangement. There will thus be recognized that the test material 1 continually contacts at one surface the ground electrode 2 and at its other surface the electrodes 4, 5 and 6. The test material, however, prior to entering the narrowmost location, previously is contacted by part of the ground electrode 5 which extends transverse to the direction of movement. Consequently, there is realized the advantage with this exemplary embodiment of the invention that the webs of the meander-shaped electrode 5 extending transverse to the direction of movement of the test material 1, act as discharge electrodes 5* and 5** resspectively, whereas at the narrowest region between the ground electrode 2 and the cylinder 32 is grounded electrode 5.

A further advantageous constructional manifestation of a part of the electrode arrangment has been illustrated in FIG. 4. Here, the electrode arrangement E" is characterized by the features that the cylinder 3' arranged above the test material 1 consists of individual disks. In this way there is realized ring-shaped electrodes. Thus, in the lengthwise direction of the cylinder 3' there are alternately arranged a disk 4' carrying positive potential, an insulating disk 32', a disk 5' carrying zero potential, an insulating disk 32', a disk 6' carrying negative potential, an insulating disk 32' and so forth. Also in this case there is brought about by the electrode 5', between the electrodes 4' and 6', carrying zero potential, a removal of harmful electrostatic charges upon entry of the test material 1 into the measuring zone.

FIG. 5 illustrates a cross-sectional view through an apparatus according to FIG. 2, wherein there have been shown an electric field 28 extending in the transverse direction of the test material 1 and two electrical fields 30 and 31 extending in the lengthwise direction of the test material. In this regard attention is again invited to FIG. 1.

While there are shown and described present preferred embodiments of the invention, it is to be distinctly understood that the invention is not limited thereto, but may be otherwise variously embodied and practiced within the scope of the following claims.

What is claimed is:

1. A method of measuring the moisture of substantially flat textile structures, especially textile webs, comprising the steps of: feeding the textile structure along a predetermined path of travel towards a measuring location where there is carried out a measuring operation, removing electrical charges from the textile structure prior to initiation of the measuring operation, carrying out the measuring operation, deriving the useful signal components of the same polarity by means of the measuring operation and dependent upon the conductance of the textile structure, deriving disturbance signal components of opposite polarity which depend upon external voltages, additively processing the useful signal components into a measurement value, and adding the disturbance signal components which by virtue of their opposed polarity at least approximately cancel one another.

2. An apparatus for measuring the moisture content of textile structures, especially textile webs, comprising an electrode arrangement for contacting the textile material defining the test material, said electrode arrangement possessing measuring electrodes for measuring the moisture content of the test material and at least one discharge electrode neighboring said measuring electrodes, said electrode arrangement further comprises a ground electrode, a further electrode which is at positive potential and at least one further electrode which is at negative potential, an amplifier arrangement having first and second inputs and comprising two direct-current series connected amplifiers, the positive potential electrode being coupled with the first input and the negative potential electrode being coupled with the second input of the amplifier arrangement.

3. An apparatus for measuring the moisture content of textile structures, especially textile webs, comprising an electrode arrangement for contacting the textile material defining the test material, said electrode arrangement possessing measuring electrodes for measuring the moisture content of the test material and at least one discharge electrode neighboring said measuring electrodes, the discharge electrode comprises a substantially meander-shaped ground electrode extending between comb-shaped electrodes defining said measuring electrodes, the meander-shaped ground electrode having webs extending transverse to the direction of movement of the test material.

* * * * *